United States Patent [19]

Crowley et al.

[11] Patent Number: 5,002,059
[45] Date of Patent: Mar. 26, 1991

[54] TIP FILLED ULTRASOUND CATHETER

[75] Inventors: Robert J. Crowley, Wayland; Mark A. Hamm, Malden; Linden A. Wint, Dorchester, all of Mass.

[73] Assignee: Boston Scientific Corporation, Watertown, Mass.

[21] Appl. No.: 385,813

[22] Filed: Jul. 26, 1989

[51] Int. Cl.⁵ .............................................. A61B 8/12
[52] U.S. Cl. .............................................. 128/662.06
[58] Field of Search ............. 128/660.09, 660.1, , 128/662.03, 662.06; 604/93, 122, 125; 29/25.35; 249/62

[56] References Cited

U.S. PATENT DOCUMENTS

| | | | |
|---|---|---|---|
| 4,181,120 | 1/1980 | Kunii et al. | 128/662.03 |
| 4,432,371 | 2/1984 | McAusland | 128/660.1 |
| 4,796,632 | 1/1989 | Boyd et al. | 128/662.03 |
| 4,815,470 | 3/1989 | Curtis et al. | 128/662.03 |
| 4,841,977 | 6/1989 | Griffith et al. | 128/662.06 |

OTHER PUBLICATIONS

Hisanaga, K. et al. "A Transesophageal Real-Time Sector Scanner with an Oil-Filled Cell", Proc. of 23rd An. Meeting of the AIUM 1978.

*Primary Examiner*—Francis Jaworski
*Attorney, Agent, or Firm*—Donald N. Halgren

[57] ABSTRACT

The present invention relates to an ultrasonic imaging catheter having an open proximal end and a closed distal end. The closed distal end contains a septum and a situs for targeting the septum. A fluid filled syringe may be insertable though the situs and the septum to fill a chamber defined by the catheter sheath and the septum, with ultrasonic transmission fluid. The chamber subsequently receives an ultrasonic image generator and receiver within the fluid filled chamber. Injection of fluid through the septum eliminates the likelihood of air bubbles forming within the chamber which otherwise damages the ultrasonic images generated thereby when that chamber is filled with fluid through the proximal end of the catheter sheath.

15 Claims, 4 Drawing Sheets

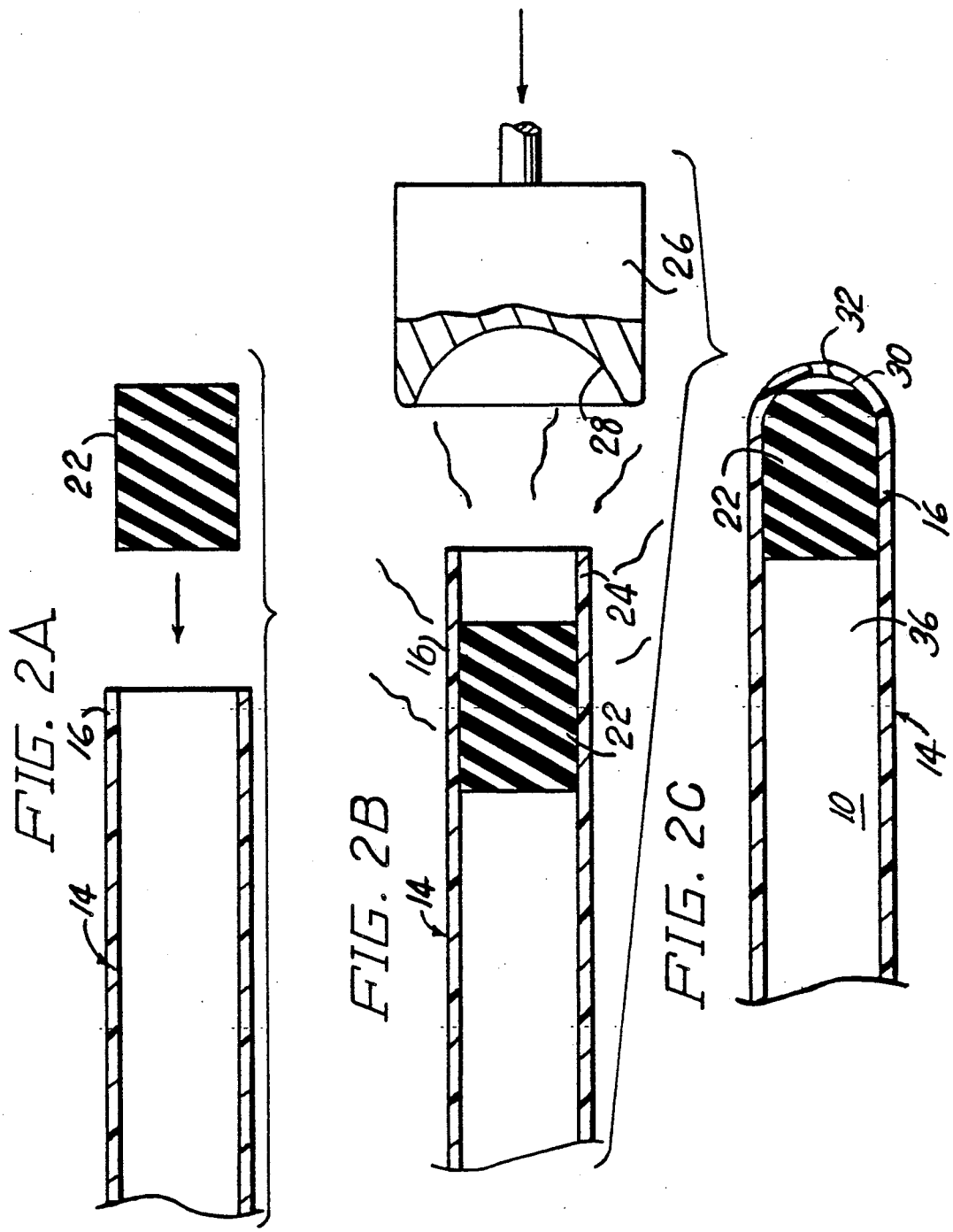

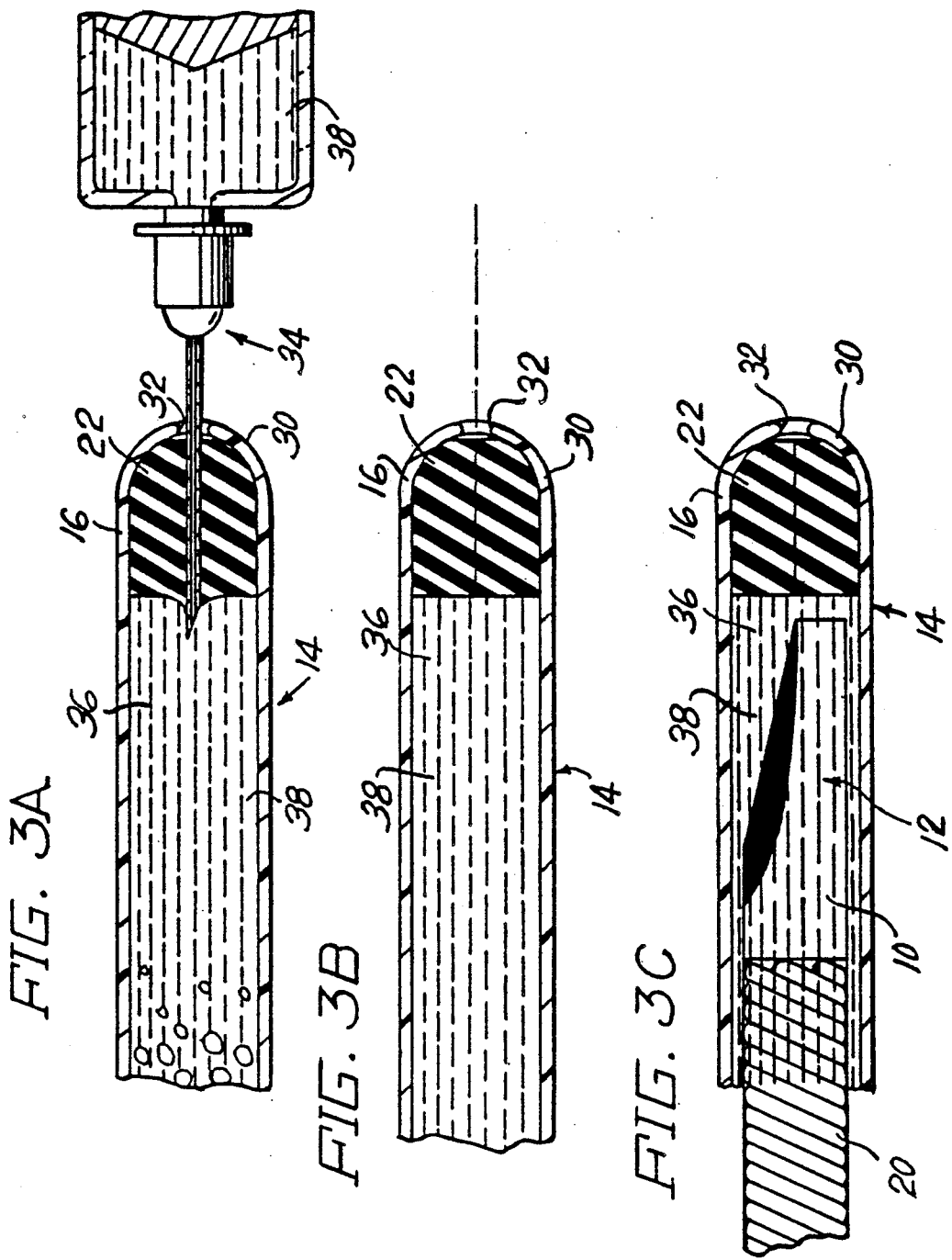

5,002,059

TIP FILLED ULTRASOUND CATHETER

BACKGROUND OF THE INVENTION (1) Field of the Invention

This invention relates to a device for diagnosing body portions with ultrasonic waves, and more particularly, to an ultrasonic catheter construction wherein a wave transmission fluid medium can be injected through a sealable plug in the distal end of the ultrasonic catheter (2) Prior Art In ultrasonic wave generating catheters, ultrasonic waves are transmitted and received through catheter walls. The catheters may be worked into various vessels of the body.

Transducers may be rotatively arranged within the catheter shaft prior to their introduction into a body. Typically, when such a device is to be utilized, a filler tube is extended into an empty catheter shaft by the operating physician. The filler tube is used to fill the catheter with ultrasonic transmission fluid such as a water, oil, or saline solution or the like.

The catheter would be permitted to overflow with this fluid, and hopefully, air bubbles would be avoided at the distal end of the catheter. The filler tube would be removed and the transducer and connecting cable inserted therein. If, however a bubble is lodged at the closed distal end of the catheter, which is likely because of the narrow passageway, it may completely spoil any image generated by the imaging catheter. This approach is also time consuming, less likely to be sterile and is a more cumbersome arrangement for providing ultrasonic catheters in medical settings.

BRIEF SUMMARY OF THE INVENTION

The present invention comprises an ultrasound imaging catheter device having a ultrasound generating and receiving means rotatably and slideably disposed therein. The device is related to that shown in a copending U.S. Pat. application Ser. No. 171,039, incorporated herein by reference. The catheter device of the present invention comprises an elongated disposable catheter sheath having a closed distal end, and an open proximal end The disposable catheter sheath is made from any acoustically transparent resiliently flexible material such as polyethylene or the like, which will permit such transparency while maintaining a sterile barrier around the ultrasound generating and receiving means. The ultrasound generating and receiving means is in electrical communication with a signal generator and receiving device for displaying the appropriate data to the operating personnel.

The distal end of the catheter sheath is arranged to receive and may be defined by a septum disposed therein, in one embodiment of the catheter device. The septum herein, is a cylindrically shaped plug manufactured from a silicone elastomer or other suitable biocompatible highly elastic material. In this first embodiment, the catheter sheath is open on both its proximal and distal ends. The septum is inserted directly into the distal end of the catheter sheath, being maintained therein by frictional engagement therewith. A slight annular portion of the distal end of the catheter sheath is arranged to extend beyond the distal end of the septum. A heated concavely shaped metallic mold tool is then mated over and against the distalmost end of the catheter sheath and enclosed septum. The catheter sheath thereby conforms to the shape of the heated mold, to lock the septum therein, by conformance of the distalmost portion of the catheter sheath to the curve of the mold, and by frictional engagement of the septum with the inner surface of the catheter sheath. The formed distalmost end of the catheter sheath then defines a small annularly shaped dimple or situs, through which the septum may be slightly exposed.

When the attending physician wishes to assemble the ultrasound imaging catheter device, he inserts a needle tipped syringe, which has been filled with the fluid, piercing into and through the septum to reach the chamber within the catheter sheath and proximal of the septum. After he has injected a sufficient amount of fluid therein, the needle may be withdrawn and the septum will be sealed by virtue of the elastic properties of the septum, and still prevent leakage, maintain sterility, and then the ultrasound generating and receiving device may then be inserted into the sheath, through its proximal end, thereby being ready for utilization with a patient with a promptness not found in the prior art. Because the needle does not appreciably fill the hollow catheter with its own bulk, the transducer may also be put in place first, if the user so desires.

In another embodiment of the catheter device, the distal end of the catheter sheath is pre-formed so as to have an extended sealed manipulable tip. In this embodiment, the septum may be placed on a mandrel, and inserted through the proximal end of the catheter sheath, until it becomes lodged in the closed distal end thereof, to provide the backup for the comparatively thin walled catheter sheath. An opening may be disposed adjacent the extended tip of the catheter sheath so as to provide a situs for the syringe in the pre-formed extended tip catheter device.

In either embodiment, upon filling of the chamber proximal to the septum, the syringe can be removed without concern for creating air or gas bubbles in that chamber. The ultrasound generating and receiving device may then be readily inserted into the catheter sheath for immediate utilization thereof with a patient awaiting examination.

BRIEF DESCRIPTION OF THE DRAWINGS

The objects and advantages of the present invention will become more apparent when viewed in conjunction with the following drawings, in which:

FIG. 2A shows a catheter sheath in first embodiment thereof, in a septum receiving condition;

FIG. 2B shows the catheter sheath and septum of FIG. 2A, mated;

FIG. 2C shows the catheter sheath and septum in a molded, pre-filled condition;

FIG. 3A shows a catheter device being filled by a needled syringe which has pierced the septum;

FIG. 3B shows the catheter device, with its chamber proximal to the septum, filled with fluid, the syringe withdrawn therefrom;

FIG. 3C shows an enlarged view of the distal end of the catheter device assembly shown in FIG. 1B.

DESCRIPTION OF THE PREFERRED EMBODIMENT

Figure 1A:
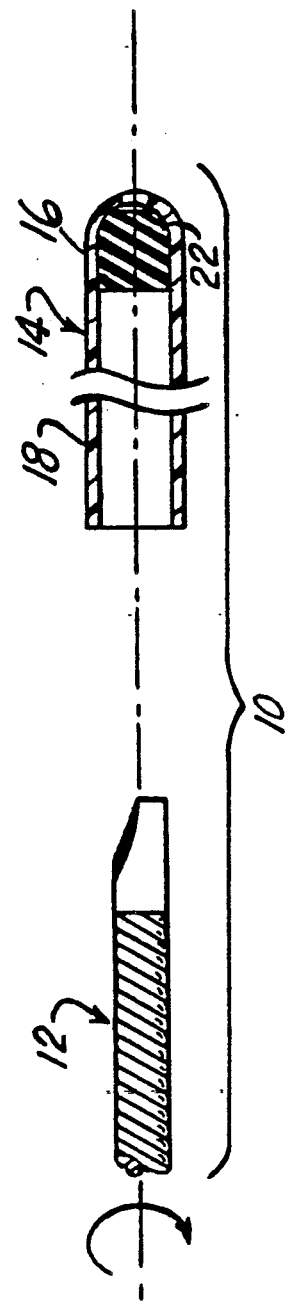
FIG. 1A shows an exploded view, partly in section, of a rotatable ultrasound generating and receiving device in axial alignment with a catheter sheath constructed according to the principles of the present invention.

Referring now to the drawings in detail, and particularly to FIG. 1A, there is shown in an exploded view, an ultrasound imaging catheter device 10, comprised of a reusable rotatable and slideably insertable ultrasound generating and receiving means 12 and a single use disposable elongated flexible catheter sheath 14, having a distal end 16, and a proximal end 18.

Figure 1B:
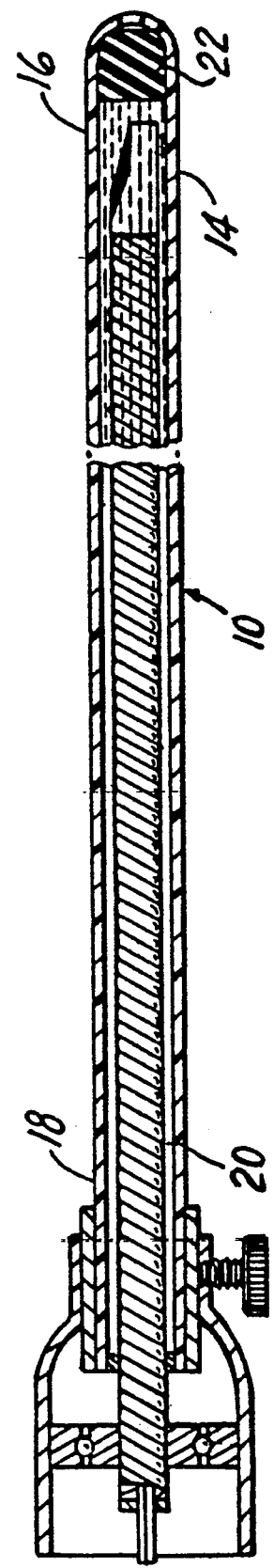
FIG. 1B shows an ultrasound imaging catheter assembly in its completed state.

The full ultrasound imaging catheter device 10, is shown assembled in FIG. 1B, showing its distal end 16 closed and its proximal end 18 open for the passage of a cable communication means 20 therethrough, in a circuit (not shown) for displaying the images returned to the catheter device 10.

Construction of the catheter sheath 14, and a septum 22 is shown in FIGS. 2A, B and C, wherein the septum 22, a cylindrically shaped plug of elastomeric material such as a silicone elastomer, e.g. the trademarked material VISILOX 1010, which is a biocompatable substance, is inserted into the distal end 16 of the catheter sheath 14, and is maintained therein by frictional engagement there between. A slight distalmost annular rim 24 becomes deformed when heated by a metal tool 26 having a concavely shaped mold 28 heated to about 300° F., in a manner indicated in FIG. 2B, to become a closed end 30 on the distal end 16 of the catheter device 10, as shown in FIG. 2C. The formed distalmost end 16 now includes an annularly shaped dimple 32 acting as a situs through which the needle tip of a syringe 34, may be inserted.

FIG. 3A shows such a syringe 34, the needle tip of which is inserted into the chamber 36 proximal of the septum 22, which needle tip extends through the elastomer septum 22. Fluid is transferred from the syringe 34, into the chamber 36, eliminating the air bubbles that otherwise are often generated by other catheter filling arrangements.

FIG. 3B shows the chamber 36 filled with the ultrasound transmission fluid 38, usually sterile water or saline solution, the opening which the tip of the syringe 34 having generated, now being closed tightly because of the elastic nature of the material comprising the septum 22, creating a fluid and air tight sterile seal.

The remaining step in the set-up of the ultrasound imaging catheter device 10, is shown in enlarged view in FIG. 3C, wherein the ultrasound image generating and receiving means 12 is slidably disposed into the catheter sheath 14, ready for insertion into the vessel of a patient, the ultrasound image generating and receiving means 12 filling the chamber 36 together with the fluid 38, in the absence of any air bubbles, which would otherwise damage the quality of images generated thereby.

Figure 4:
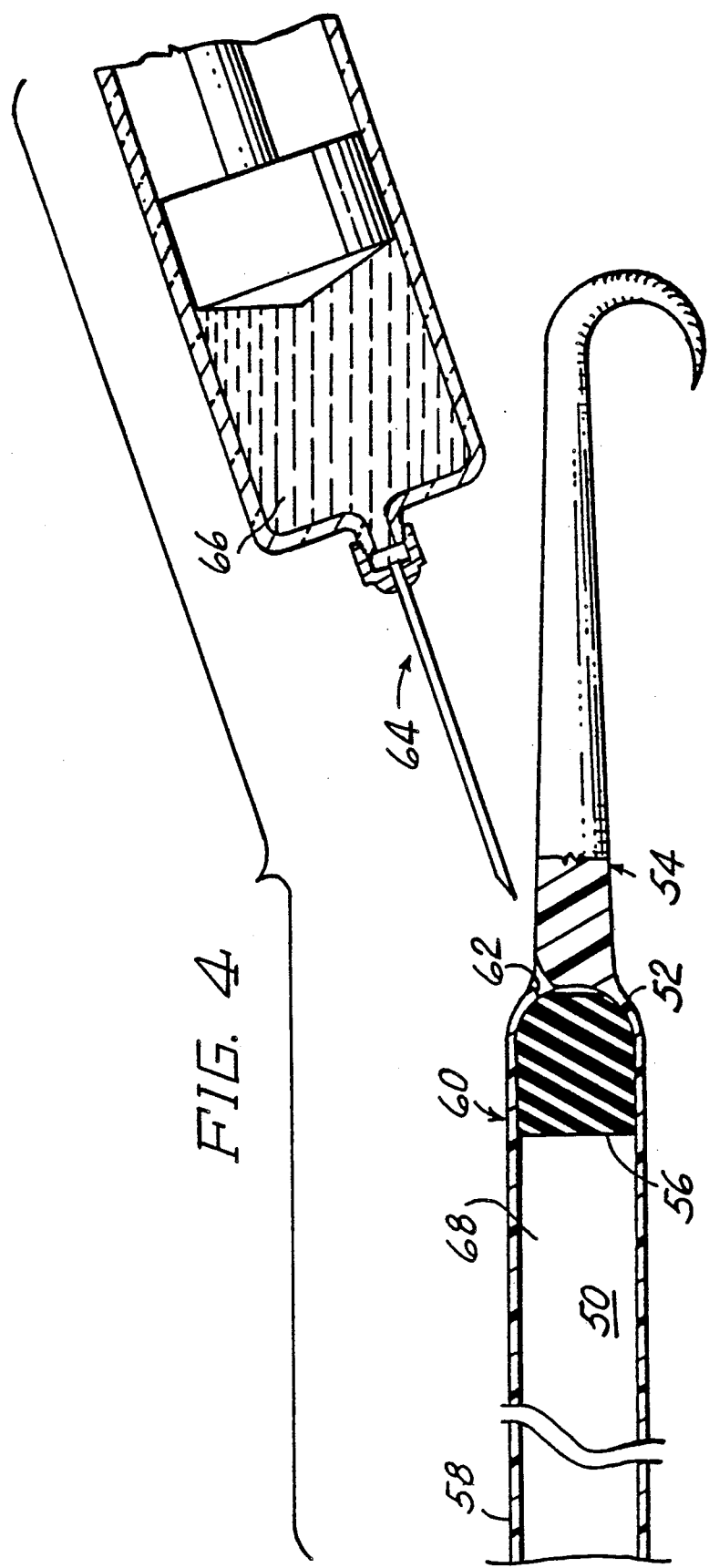
FIG. 4 is a side elevational view of a further embodiment of the catheter device, having a pre-formed manipulable tip.

A further embodiment of an ultrasound imaging catheter device 50 is shown in FIG. 4, wherein the device 50 has a distal end 52 having a closed pre-formed extended manipulable tip 54 molded as part of said sheath 60. In this embodiment, a septum 56 may be placed on an extended shaft such as a mandrel, not shown, and inserted through the proximal end 58 of the catheter sheath 60, until it becomes lodged within the closed distal end 52 thereof, to provide backup for the comparatively thin walled catheter sheath 60.

An opening 62 may be arranged eccentrically adjacent the extended tip 54, so as to provide a situs for the tip of a syringe 64 which will inject ultrasound transmission fluid 66 through the exposed septum 56, and into the chamber 68 proximal thereto, in the catheter device 50. Then, upon appropriate filling of the chamber 68, the needle of the syringe 64 may be withd rawn from the septum 56 without concer for the generation of air bubbles therein. A reusable ultrasound generating and receiving device, similar to FIG. 1A, may then be inserted into the catheter sheath 60 for immediate utilization thereof, in a patient awaiting examination.

I claim:

1. A device for diagnosing body interiors utilizing the transmission and receiving of ultrasonic waves generated therewithin, said device comprising:

an elongated catheter sheath formed of a ultrasonically transmissible material having a patient insertable distal end and a proximal end;

an elastomeric septum arranged within said distal end of said elongated catheter sheath to define a chamber with respect to said catheter sheath and the distal end of said septum;

a situs arranged at the distal end of said sheath, through which a syringe needle may be inserted for the injection of fluid into said chamber, to permit fluid entry into said chamber, while eliminating the likelihood of bubbles formed therein which would hinder proper ultrasonic patient examination.

2. A device for diagnosing body interiors as recited in claim 1, wherein said septum comprises a cylindrically shaped plug of elastomeric material.

3. A device for diagnosing body interiors as recited in claim 1 wherein said situs comprises an opening in said catheter sheath which provides a target for a syringe needle to be directed thereat.

4. A device for diagnosing body interiors as recited in claim 1, wherein said septum and said situs are contiguous to one another.

5. A device for diagnosing body-interiors as recited in claim 1, wherein said distal end of such sheath includes a preformed extended manipulable tip, molded as part of said sheath.

6. A device for diagnosing body interiors as recited in claim 5, wherein said situs is eccentrically disposed on the distal end of said sheath, adjacent said extended tip.

7. A device for diagnosing body interiors as recited in claim 6, wherein said situs comprises an opening through said sheath, exposing said septum.

8. A method of manufacturing a device for diagnosing body interiors utilizing the transmission and receiving of ultrasonic waves generated therewithin, comprising the steps of:

providing an elongated flexible sheath having a patient insertable distal end and a proximal end;

inserting a plug of elastomeric material into the distal end of said elongated sheath; and arranging a situs on the distal end of said sheath for the insertion of a syringe needle therethrough.

9. The method of manufacturing a device for diagnosing body interiors as recited in claim 8, including the step of:

molding the distalmost portion of said catheter sheath around said plug using heat and/or pressure, so as to form said situs.

10. The method of manufacturing a device for diagnosing body interiors as recited in claim 8, including the step of:

extending said situs through said catheter sheath so as to expose said septum.

11. The method of manufacturing a device as recited in claim 10, including the step of:
arranging the situs eccentrically on the distal end of said catheter sheath, adjacent an extended preformed manipulable tip thereon.

12. The method of manufacturing a device for diagnosing body interiors as recited in claim 8, including the step of:
inserting said plug of elastomeric material into said distal end of said catheter sheath, through the proximal end of said catheter sheath.

13. The method of manufacturing a device for diagnosing body interiors as recited in claim 12, including the step of:
arranging said plug on the end of a mandrel for insertion thereof into the distal end of said catheter sheath.

14. A method of assembling a device for diagnosing body interiors utilizing the transmission and receiving of ultrasonic waves generated therewithin, comprising the steps of:
providing an elongated flexible catheter sheath having a proximal end and a closed patient insertable distal end, said closed distal end having an elastomeric plug septum disposed therein, said plug and said catheter sheath defining a chamber therewith;
arranging a situs on the distal end of said catheter sheath;
inserting a syringe needle into said situs and through said septum to permit said chamber to be filled with a fluid injected therein from said syringe.

15. The method of assembling a device for diagnosing body interiors as recited in claim 14, including the step of:
withdrawing the syringe needle from the septum and situs to permit the distal end of the catheter sheath to seal itself closed.

* * * * *